United States Patent
Hartmann et al.

(10) Patent No.: US 7,357,989 B2
(45) Date of Patent: Apr. 15, 2008

(54) DI(HET)ARYLAMINOTHIAZOLE DERIVATIVES AND THEIR USE IN ORGANIC LIGHT-EMITTING DIODES(OLEDS) AND ORGANIC PHOTOVOLTAIC COMPONENTS

(75) Inventors: Horst Hartmann, Merseburg (DE); Andreas Kanitz, Hoechstadt (DE); Wolfgang Rogler, Mohrendorf (DE); Jorg Schumann, Erlangen (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 0 days.

(21) Appl. No.: 10/343,992

(22) PCT Filed: Aug. 7, 2001

(86) PCT No.: PCT/DE01/03016

§ 371 (c)(1), (2), (4) Date: Feb. 6, 2003

(87) PCT Pub. No.: WO02/12212

PCT Pub. Date: Feb. 14, 2002

(65) Prior Publication Data

US 2004/0028943 A1    Feb. 12, 2004

(30) Foreign Application Priority Data

Aug. 7, 2000    (DE)    ................ 100 38 437

(51) Int. Cl.
  *H01J 1/62*    (2006.01)
  *C09K 11/06*    (2006.01)
(52) U.S. Cl. .................. 428/690; 428/917; 257/40; 257/102; 257/103; 313/504; 313/506
(58) Field of Classification Search ............... 428/690, 428/917; 313/504, 503, 506, 509; 257/40, 257/E51.04, 102, 103; 514/361, 370, 252, 514/256, 324, 648
See application file for complete search history.

(56) References Cited

U.S. PATENT DOCUMENTS

| | | | |
|---|---|---|---|
| 3,467,666 A | 9/1969 | Dexter et al. | ............ 260/306.8 |
| 4,539,507 A | 9/1985 | VanSlyke et al. | |
| 5,247,190 A | 9/1993 | Friend et al. | |
| 6,280,859 B1 * | 8/2001 | Onikubo et al. | ............ 428/690 |
| 6,586,453 B2 * | 7/2003 | Dhanoa et al. | ............ 514/365 |

FOREIGN PATENT DOCUMENTS

| | | | |
|---|---|---|---|
| DE | 41 22 563 | | 9/1993 |
| EP | 0 866 110 | | 9/1998 |
| GB | 1 185 327 | | 3/1970 |
| GB | 1185327 | | 3/1970 |
| JP | 63280255 | | 11/1988 |
| JP | A 3-163189 | | 7/1991 |
| JP | 09077854 A | | 3/1997 |
| WO | WO 97-03073 | * | 1/1997 |
| WO | 98/20565 | | 5/1998 |

OTHER PUBLICATIONS

Wang-Lin Yu et al., "New Efficient Blue Light Emitting Polymer for Light Emitting Diodes," Chem. Commun., 1999, pp. 1837-1838.
Römpp Chemie Lexikon, 9. Edition, pp. 1750 and 4796.
Katrin Eckert et al., "Preparation and Characterization of Cyanovinyl-Substituted 2-Aminothiophenes and 2-Aminothiazoles and Some of Their Heterooligomers," Eur. J. Org. Chem., 2000, pp. 1327-1334.
Chemical Abstracts, V. 128, 1998, p. 597 (62069z).
Chemical Abstracts, V. 127, 1997, p. 1200 (254954k).
Chemical Abstracts, V. 126, 1997, p. 613 (251686t).
Database WPI, Section Ch, Week 198901, Derwent Publications Ltd., London, GB: AN 1989-003179, XP002186877- & JP 63280258 A (Mitsubishi Paper Mills Ltd), Nov. 17, 1988 (abstract).

* cited by examiner

*Primary Examiner*—Terrel Morris
*Assistant Examiner*—Camie S. Thompson
(74) *Attorney, Agent, or Firm*—Young & Thompson

(57) ABSTRACT

Novel 4,5-di(het)aryl-substituted 2-(N,N-di(het)arylamino)-thiazole derivatives of general structure (a), whereby the following applies: $R^1$, $R^2$ and $R^3$ and $R^4$, independent of one another, are each a monofunctional (het)aryl system; $R^1$ can additionally be a corresponding bifunctional (het)arylene system; $R^3$ can additional signify $R^7$, whereby $R^7$ represents a chemical bond or a bifunctional (het)arylene system, or $R^3$ can be one of the following groupings (b) and (c); $R^7$ represents a chemical bond or a bifunctional (het)arylene system, and; $R^4$ can also be H or (d).

9 Claims, No Drawings

DI(HET)ARYLAMINOTHIAZOLE DERIVATIVES AND THEIR USE IN ORGANIC LIGHT-EMITTING DIODES(OLEDS) AND ORGANIC PHOTOVOLTAIC COMPONENTS

The invention relates to novel di(het)arylaminothiazole derivatives, i.e. diarylaminothiazole or dihetarylaminothiazole derivatives ("hetaryl"="heteroaryl"), and the preparation and use thereof.

For organic light-emitting diodes (organic LEDs=OLEDs) and organic photovoltaic components, organic materials which are capable of electroluminescence are required. These may be either compounds having a small molecular size (cf. for example U.S. Pat. No. 4,539,507) which are vaporizable or polymeric materials (cf. for example U.S. Pat. No. 5,247,190) which can be processed by spin-coating.

The synthesis of compounds of said type requires aromatic coupling reactions. Some of such reactions, in which halogen-containing compounds are used, take place under metal catalysis, for example by a Heck reaction or by a Suzuki reaction (in this context, cf.: "Chem. Commun.", 1999, pages 1837 to 1838). However, it is scarcely possible to remove the metal, such as palladium (in this context, cf.: "Römpp Chemie-Lexikon", 9th edition, page 1750), completely thereby. However, metals—and also traces of incompletely converted halogen-containing intermediates—act as so-called quenchers, i.e. they quench electroluminescence in their environment and they therefore greatly reduce the efficiency of the materials prepared.

In an aromatic coupling corresponding to an Ullmann reaction (in this context, cf.: "Römpp Chemie-Lexikon", 9th edition, page 4796), the formation of byproducts and of crack products, which are the result of high process temperatures, is a major problem. In fact, the purification of the reaction product to an acceptable extent is scarcely possible here, if at all.

The invention extends the range of the charge transport materials, particularly for the production of charge transport cascades, and is derived from the patent DE 10002424.6.

The invention therefore relates to novel 4-substituted 2-(N,N-di(het)arylamino)thiazole derivatives of the general structure

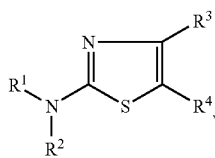

in which the following applies:

$R^1$, $R^2$ and $R^3$—independently of one another—are each a monofunctional (het)aryl system, i.e. a conjugated carbocyclic or heterocyclic ring system, which may also comprise linearly or angularly fused or linked identical or different ring types, it being possible for the peripheral hydrogen atoms optionally to be substituted by alkyl, alkoxy, phenoxy, dialkylamino or diphenylamino groups (alkyl=$C_1$ to $C_6$);

the following (het)aryl systems are preferred:
phenyl, biphenyl, alkylphenyl, alkoxyphenyl, phenoxyphenyl, naphthyl, anthryl, phenanthryl, 4-trityphenyl, thienyl, thiazolyl, benzothiazolyl, pyridyl, quinolyl, isoquinolyl, pyridazinyl, pyrimidinyl, quinazolyl, pyrazinyl, quinoxazyl, phenazinyl and pyrenyl systems.

$R^1$ may furthermore be a corresponding bifunctional (het)arylene system, i.e. a conjugated carbocyclic or heterocyclic ring system, which may also comprise linearly or angularly fused or linked identical or different ring types, it being possible for the peripheral hydrogen atom optionally to be substituted by alkyl, alkoxy, phenoxy, dialkylamino or diphenylamino groups (alkyl=$C_1$ to $C_6$);

the following (het)arylene systems are preferred:
phenylene, biphenylene, alkylphenylene, alkoxyphenylene, phenoxyphenylene, napthylene, anthrylene, phenanthrylene, thienylene, thiazolylene, pyridazinylene, phthalazinylene and pyrazinylene systems.

$R^1$ and $R^2$ together may also form a 10-phenothiazinyl, 10-phenoxazinyl or 9-carbazolyl group.

$R^3$ may furthermore be $R^7$, $R^7$ being a chemical bond or a bifunctional (het)arylene system, or $R^3$ may be one of the following groups:

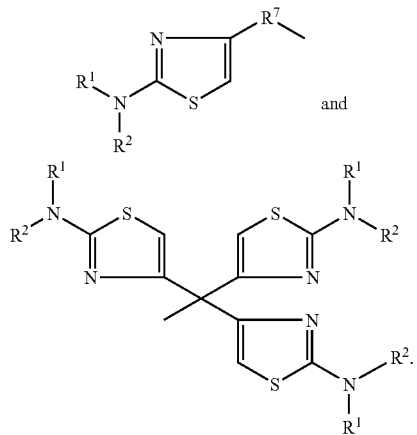

$R^7$ being a chemical bond or a bifunctional (het)arylene system;
$R^4$ may also be H or

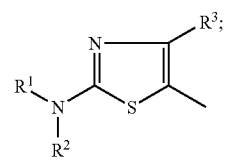

the following may furthermore be the case:
$R^3$ and $R^4$ together form one of the following groups:

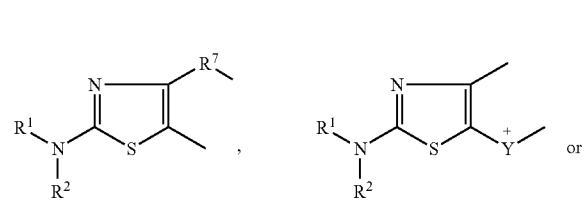

-continued

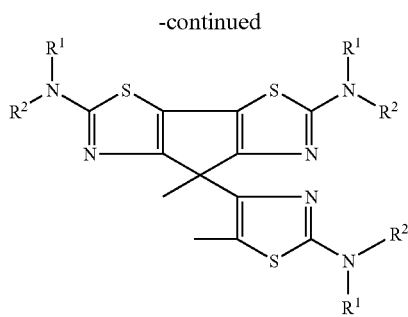

$R^3$ together with $R^1$ forms the following polymer segment:

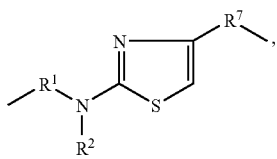

$R^4$ together with $R^1$ forms the following polymer segment:

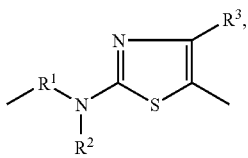

$R^4$ and $R^3$ together with $R^1$ form the following polymer segments:

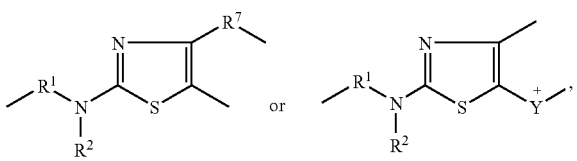

Y in each case being CH or N.

The preparation of the novel di(het)arylaminothiazole derivatives is effected by means of a hetaryl cyclization reaction under mild conditions and without metal catalysts. These compounds can thus be prepared in high purity, i.e. the efficiency of these materials, in particular the electroluminescence, is not adversely affected by impurities which are present in compounds prepared by known processes, for example owing to the catalyst used. A further advantage of these materials consists in improved redox properties adaptable to the respective purpose and due to the variety of structural possibilities which arises from the structural principle described in more detail below. This structural principle furthermore enables the novel materials to be obtained without problems also in the form of oligomer and polymer structures, i.e. for oligo- and polyaminothiazole derivatives to be prepared, and the maximum degree of polymerization of n=100 cannot be exceeded owing to the stepwise condensation.

The synthesis of the novel compounds requires in some cases precursors which have been unknown to date. However, these precursors are obtainable—from commercially available starting materials—in virtually quantitative yield.

Preparation of the thiourea starting materials:

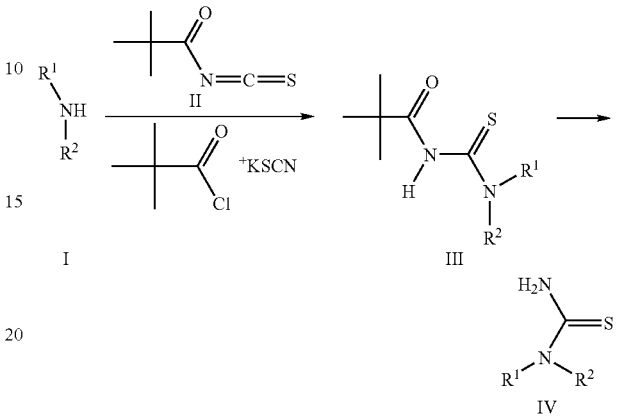

Preparation of the thiazole derivatives:

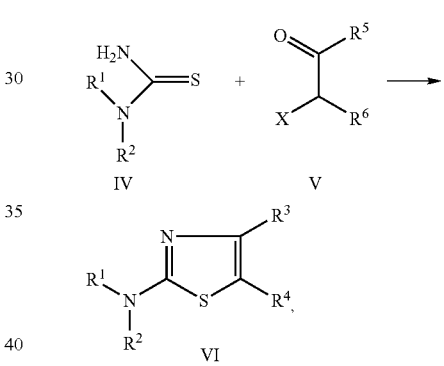

The following applies here:

$R^1$, $R^2$, $R^3$ and $R^4$ have the abovementioned meanings;

$R^5$ and $R^6$—independently of one another—are each a monofunctional (het)aryl system, i.e. a conjugated carbocyclic or heterocyclic ring system, which may also comprise linearly or angularly fused or linked identical or different ring types, it being possible for the peripheral hydrogen atoms optionally to be substituted by alkyl, alkoxy, phenoxy, dialkylamino or diphenylamino groups (alkyl=$C_1$ to $C_6$);

$R^5$ may furthermore be the group $R^8$, the compound V carrying a group —CO—CH$_2$X, where X is halogen, preferably Cl, Br or I, at the free bond, or $R^5$ may be a group —C(CO—CH$_2$X)$_3$.

$R^6$ may also be hydrogen.

The first stage of the synthesis of the thiazole derivatives comprises the reaction of a secondary amine I with pivaloyl isothiocyanate II to give an N,N-disubstituted pivaloylthiourea III. The reaction is carried out in a suitable solvent, preferably acetone, at elevated temperature, preferably in the region of the boiling point of the solvent, under inert gas. As a rule, the product need not be isolated and is then converted, in a second stage, in aqueous hydrochloric acid, into the N,N-disubstituted thiourea IV.

In a third stage, the N,N-disubstituted thiourea IV—depending on the substitution pattern (cf. IVa and IVb below)—is converted by reaction with an α-haloacyl compound V in a suitable solvent, preferably acetic anhydride, dimethylformamide or ethanol, into a semiconducting 4-substituted 2-(N,N-di(het)arylamino)-thiazole derivative VI, according to the substitution pattern of the acyl compound (cf. Vb to Vd below). This is effected by a primary S-alkylation and a subsequent cyclization (ring closure reaction) and aromatization according to the "Hantz thiazole synthesis". Cyclization can also be accelerated by adding a deprotonating agent, preferably triethylamine.

Thiazole derivatives VI which are unsubstituted in the 5-position, i.e. $R^4$=H, can be converted by oxidative coupling into dimeric or polymeric derivatives VI (cf. VIe, f, i, m, n, p, s below), which are likewise organic semiconductor materials. The oxidative coupling is effected in a suitable solvent, preferably dry tetrahydrofuran, by oxidizing agents known per se, preferably by oxidation of the respective lithium-complexed thiazole derivative—prepared by means of butyllithium—with copper(II) chloride or by electrooxidation on a conductive substrate, for example on a glass sheet coated with ITO (ITO=indium tin oxide)

By means of halogenated 1,2-diketones (cf. Vd/d below)—as an α-haloacyl compound—thiazole derivatives VI prepared from the thioureas IV and unsubstituted in the 5,5'-position and bonded in the 4,4'-position (cf. VIq and VIr below) can be converted with orthoformic ester or with nitrous acid, which is generated, for example, from sodium nitrite or isoamyl nitrite, into corresponding cationic hole transport materials (cf. VIt and VIu below), which are similar to the known polythiophenes and polyanilines in their properties as organic conductors.

The structural formulae of a relatively large number of the novel thiazole derivatives—together with the direct starting materials—are reproduced in the form of a table below.

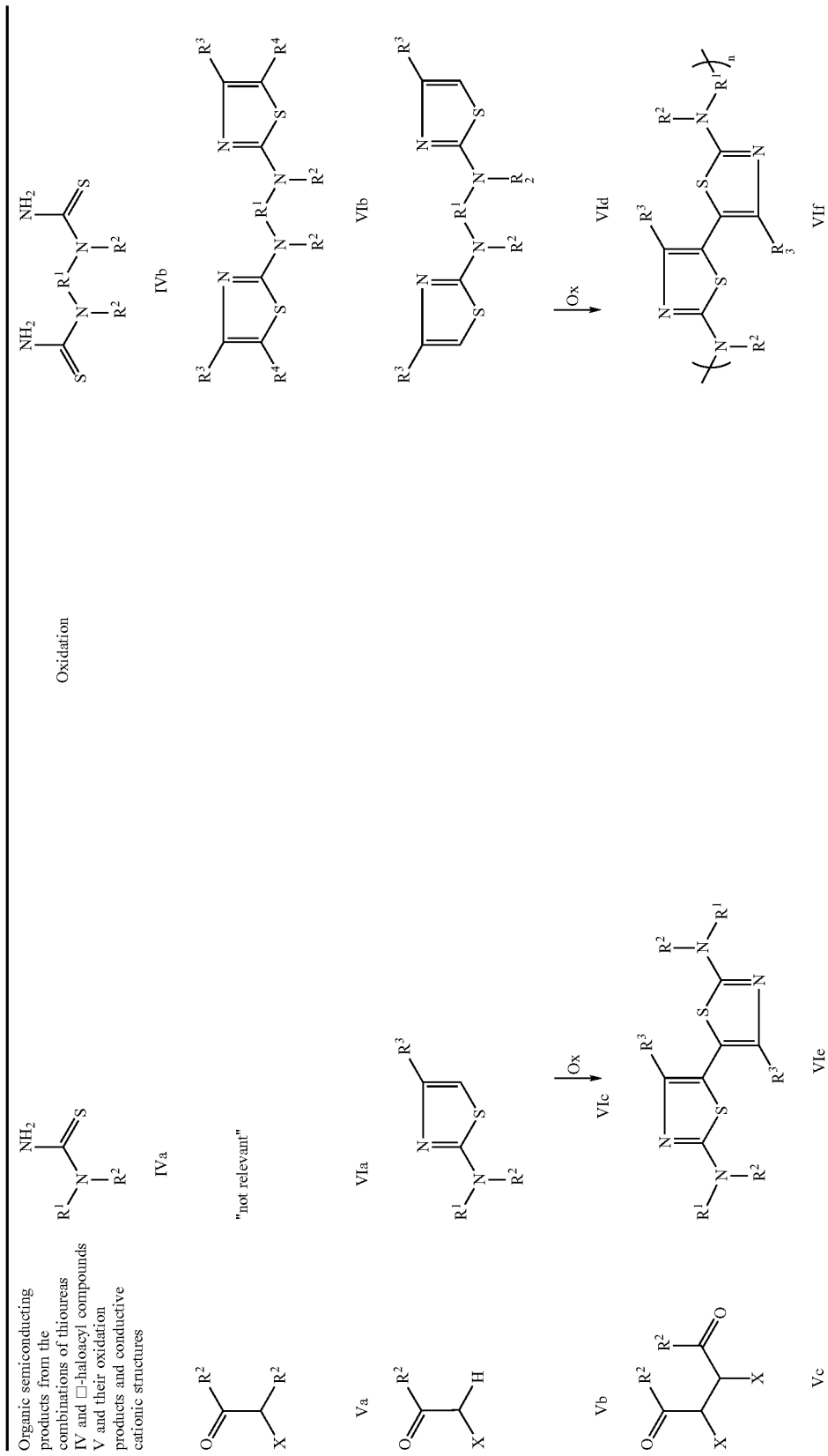

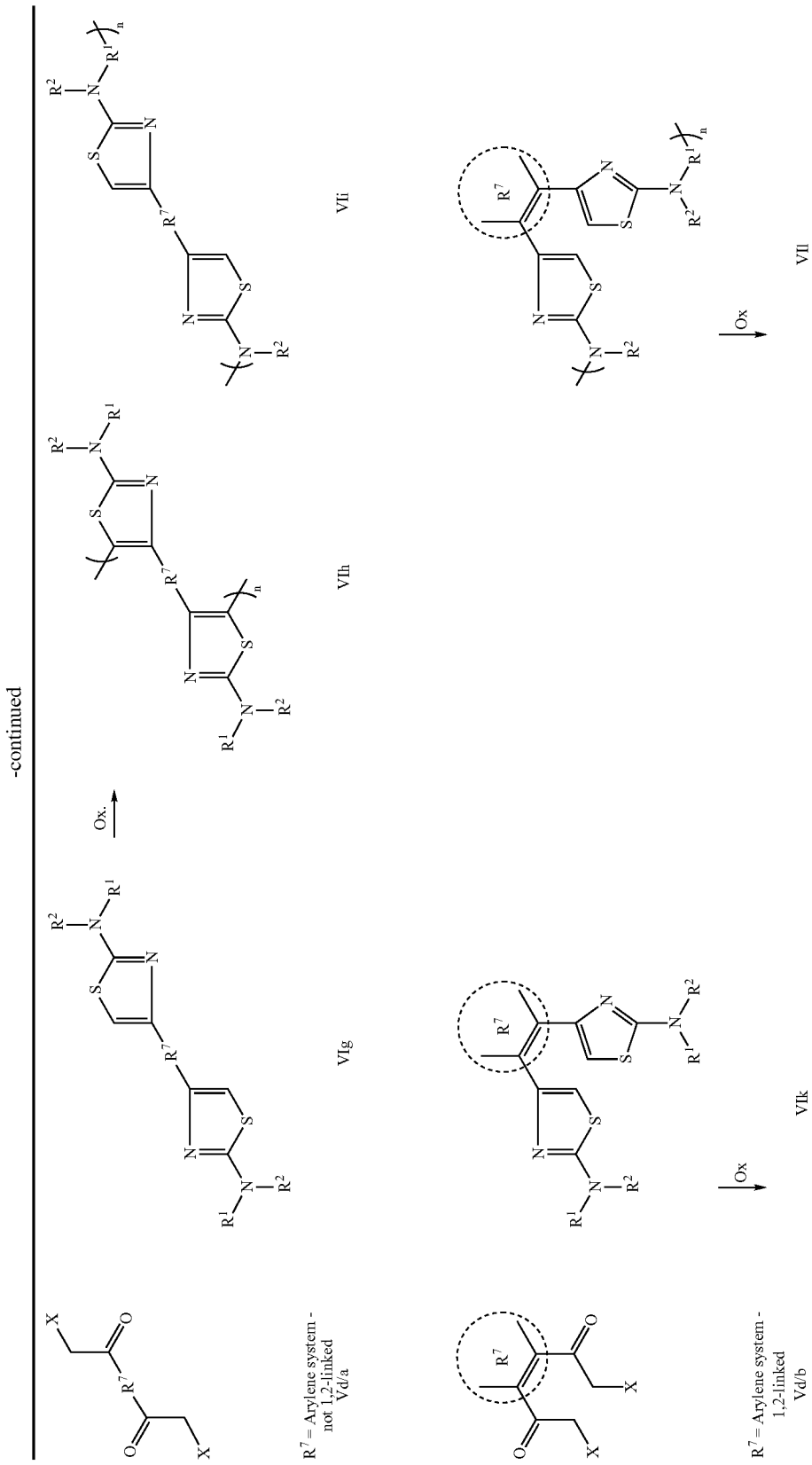

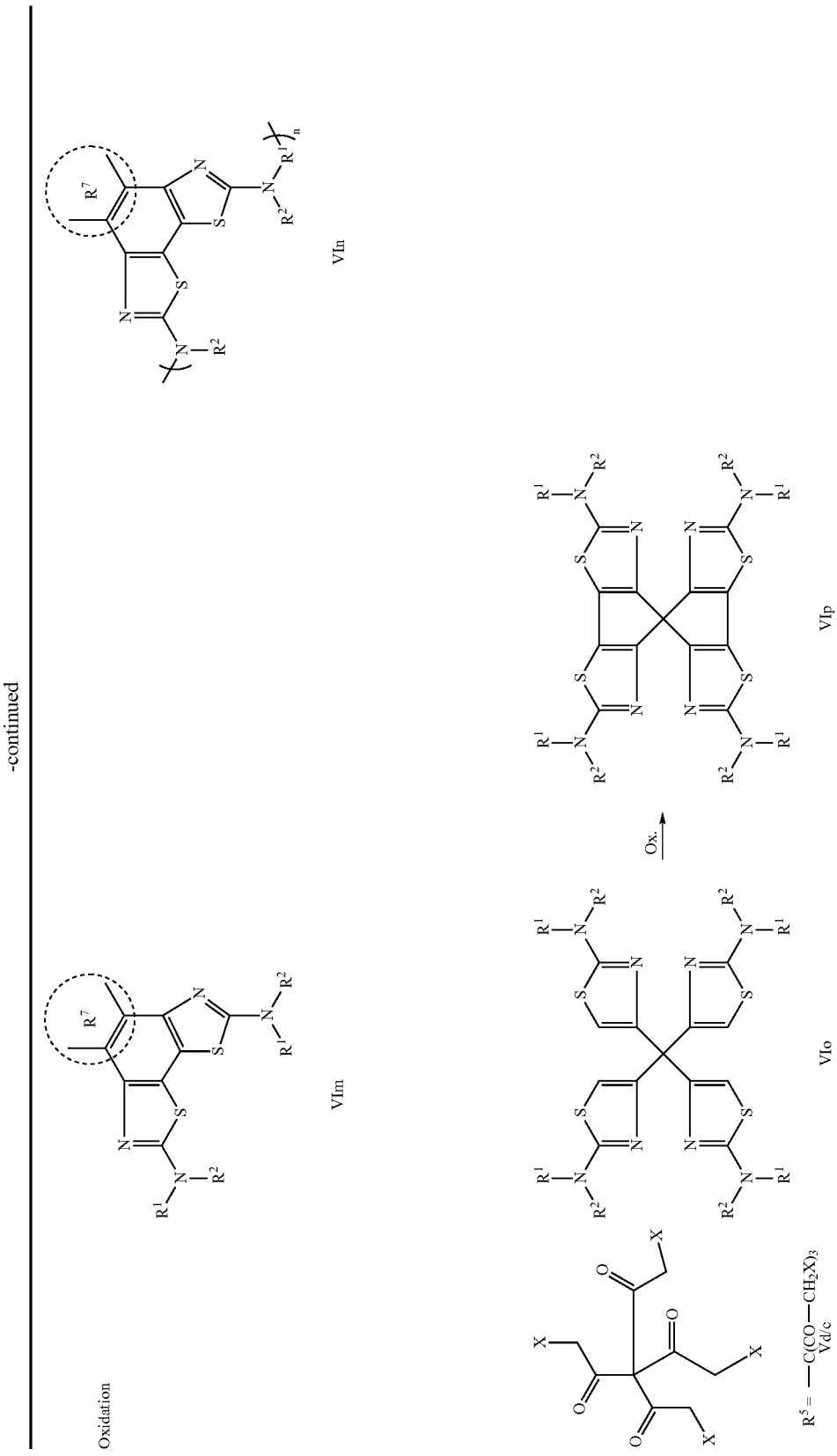

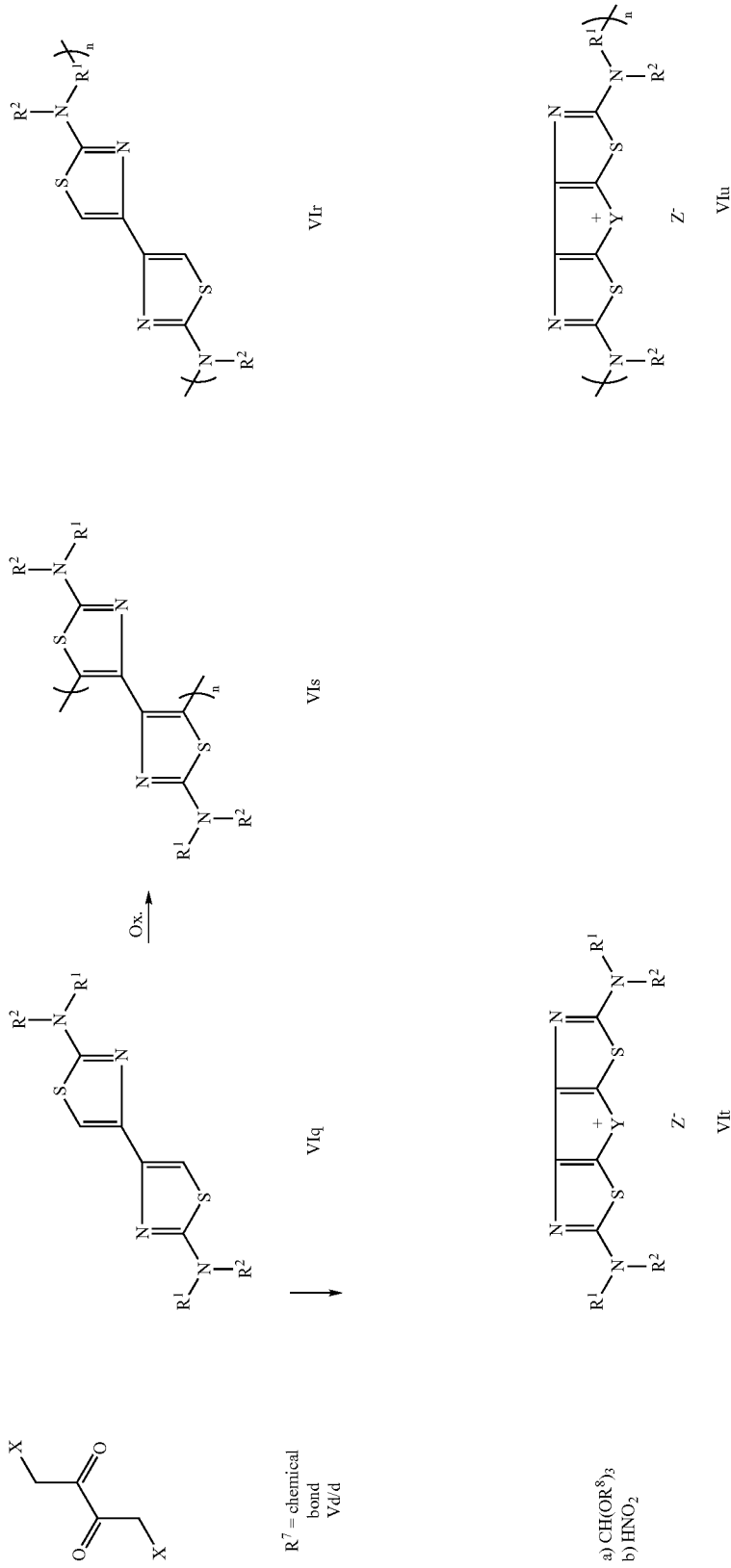

$R^6$ is an alkyl radical having 1 to 5 C atoms, $Z^-$ is any desired anion, preferably a polystyrenesulfonate or another organic sulfonate, n is in each case an integer from 2 to 100, on average a degree of polymerization n=20 to n=40 being reached.

The thiazole derivatives according to the invention of type VI are all suitable materials for the production of organic light-emitting diodes (OLEDs) and organic photovoltaic components or cells. They can be used both in hole transport layers or layer cascades and in emitter and electron transport layers. The respective layer position in OLEDs is determined in particular by the (het)aryl or (het)arylene members: the more of these members which have a π-electron deficiency, i.e. so-called π-deficient aromatics, the more suitable are the thiazole derivatives as emitter and electron transport materials.

The following compound types are particularly preferred:—VIb, VId, VIe, VIf, VIg, VIm, VIp, VIt and VIu.

OLED materials which are suitable as vaporizable compounds for so-called "small molecule devices" and polymer materials processible by spin-coating and intended for so-called "polymer devices" can be realized by the synthesis route described; the nonpolymeric materials can likewise be processed by spin-coating. Owing to the common parent structure of all the materials, corresponding copolymers having tailored electronic properties can also advantageously be prepared. It is furthermore possible to realize the electronic properties required for the respective intended use by means of mixtures of corresponding materials, which—owing to the structural similarity—are very compatible with one another.

Materials tailored in this manner therefore permit a single-layer structure of OLEDs, which is very advantageous. By the additional use of the materials described in the patents DE 10002423.8 and DE 10002424.6 for optimum charge transport cascades, it is possible to realize OLEDs having a lower operating voltage (onset 2.5-3 V). Also noteworthy are the glass transition temperatures of the charge transport and emitter materials prepared in the manner described, which temperatures are very high compared with known carbocyclic charge transport materials and are in general from about 50 to 100° C. higher than those of the analogous carbocyclic compounds which, with exceptions, have a glass transition temperature of from 100° C. to 150° C. The thiazole derivatives according to the invention have a glass transition temperature of at least 180° C., preferably of at least 200° C., in particular in the range from 230 to 250° C.

The invention is to be explained in more detail with reference to embodiments.

EXAMPLE 1
Synthesis of the Pivaloylthioureas III 1 mol of potassium thiocyanate in 500 ml of absolute acetone is initially introduced into a 2 l three-necked flask having a reflux condenser, a magnetic stirrer, dropping funnel and inlet gas flow, and 1 mol of pivaloyl chloride is added dropwise. Thereafter, refluxing is effected for one hour and the respective equivalent amount of the corresponding secondary amine I (monofunctional 1 mol, bifunctional 0.5 mol), dissolved or suspended in 300 ml of acetone, is then added dropwise. The reaction mixture is then refluxed until amine is no longer detectable by thin-layer chromatography. The reaction solution is then cooled and is stirred into at least twice the amount of dilute, aqueous hydrochloric acid. The aqueous phase is separated off and discarded, and the crude product can be immediately further processed. N,N'-Diphenyl-N,N'-di(thioform-pivaloylamido)-1,4-phen-ylenediamine having a melting point of 165° C. is prepared in this manner, for example from N,N'-diphenyl-1,4-phenylenediamine, pivaloyl chloride and potassium thiocyanate.

EXAMPLE 2

Synthesis of N,N-Disubstituted Thioureas IV

The corresponding pivaloylthiourea are suspended in conc. hydrochloric acid in a beaker. 400 ml of conc. hydrochloric acid should be metered for 1 mol of pivaloyl group to be eliminated. The reaction mixture is heated to the boil until the resulting frothing has ended. It is then poured onto ice, the product separating out. The product is filtered off with suction and is recrystallized from ethanol.

The yield in each case is at least 80%.

For example, the thiourea IVa ($R^1=R^2$=phenyl) having a melting point of 212° C. is prepared in this manner.

EXAMPLE 3

Synthesis of Thiazole Derivatives VI a)

0.1 mol of the respective N,N-disubstituted thiourea IV are dissolved, together with an equivalent amount of an α-haloacyl compound V, in 200 ml of DMF in a flask provided with a stirrer and reflux condenser, after which heating is effected at 100° C. for 1 h. Thereafter, 0.1 mol of triethylamine are added and heating is effected for a further 30 min. After cooling, the thiazole derivative formed is isolated by precipitating with methanol, in some cases also with ice water, and filtering off with suction. The crude product is purified by recrystallization from ethanol. The yield in each case is from 60 to 80%.

For example, the thiazole derivative VIb ($R^1$=1,4-phenylene and $R^2=R^3=R^4$=phenyl) is prepared from the bifunctional thiourea IVb ($R^1$=1,4-phenylene and $R^2$=phenyl) and desyl chloride (α-chloro-α-phenylacetophenone) in this manner.

m.p.=300° C., MS: MH$^+$=731, T(g)=240° C. $^1$H-NMR: (DMF-D$_7$ a) 7.65 ppm (s) 4H b) 7.35 ppm (d) 4H c) 7.62 ppm (d) 4H

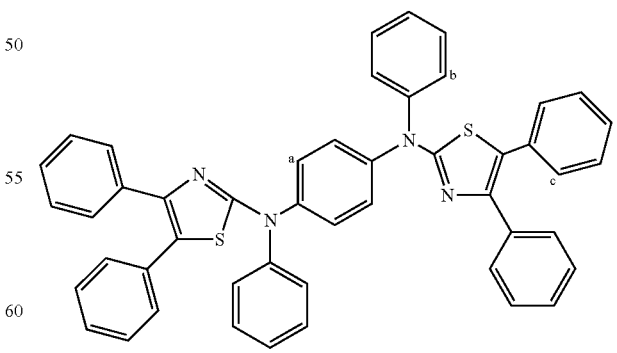

VIb b)

The following procedure is adopted for the preparation of polymeric thiazole derivatives VI, for example VIf ($R^1$=1,4-phenylene and $R^2=R^3$=phenyl):

0.1 mol of bifunctional thiourea IVb ($R^1$=1,4-phenylene, $R^2$=phenyl) are dissolved, together with 0.1 mol of dimeric phenacyl bromide Vc ($R^2$=phenyl), in 200 ml of DMF in a flask provided with a stirrer and reflux condenser, after which heating is effected at 100° C. for 1 h. Thereafter—for capping the end groups—a monofunctional thiourea IVa and a monofunctional acyl halide Va are added in succession, in the present case first 0.01 mol of N,N-diphenylthiourea and after 60 min 0.01 mol of phenacryl bromide. After a further 60 min, 0.1 mol of triethylamine are added and the mixture is allowed to cool after a further 15 min, the polymeric thiazole derivative formed being precipitated. The further working-up is effected in the manner described above; yield: about 80%.

$^1$H-NMR: (DMF-D$_7$
c) 7.1 ppm (s) 4H
d) 6.9 ppm (t) 2H
e) 7.3 ppm (t) 2H

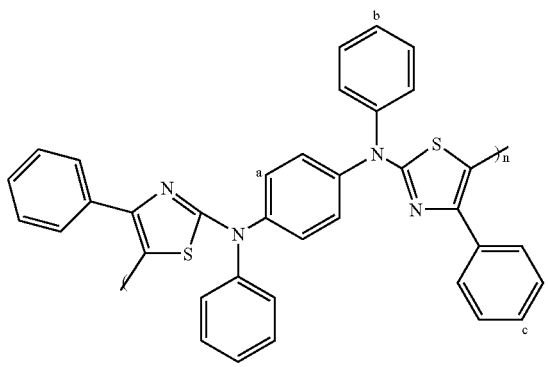

EXAMPLE 4

Synthesis of Dimeric or Polymeric Thiazole Derivatives VI (by Oxidative Coupling)

0.01 mol of a thiazole derivative VI unsubstituted in the 5-position are dissolved in 100 ml of dried THF in a flask provided with a reflux condenser, stirrer, solids metering means and inert gas flow. The mixture is cooled to −60° C., after which 0.015 mol of butyllithium are added. Thereafter, the cooling is removed and the reaction mixture is allowed to thaw to −10° C. Thereafter, 0.011 mol of copper(II) chloride are added by the solids metering means, and heating is then continued up to 40° C. The reaction is stopped after 30 min by precipitating the product with water (in the case of polymers, with methanol with addition of 10% of water) and then filtering it off with suction. The product is purified with repeated dissolution in THF and precipitation with methanol. Nonpolymeric compounds can also be purified by sublimation.

For example, the dimeric thiazole derivative VIe ($R^1$=$R^2$=$R^3$=phenyl) is prepared from 2-diphenylamino-4-phenylthiazole VIc in this manner. M.p.: 255-258° C., MS: MH+=655, and the polymer VIf already prepared in example 3b.

$^1$H-NMR: (CDCl$_3$)
a) 7.21 ppm (d) 8H
b) 7.68 ppm (d) 4H

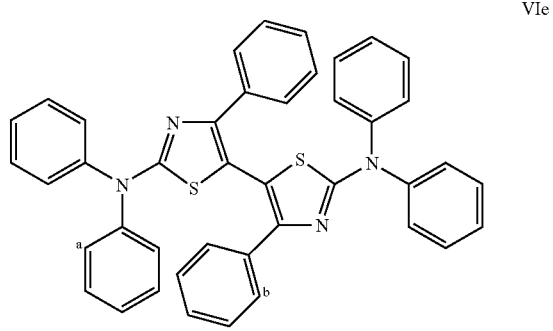

EXAMPLE 5

Synthesis of Thiazole Derivatives VI in the Form of Cationically Conductive Materials (Y=CH)

0.01 mol of a dimeric thiazole derivative VIq or VIr bonded in the 4,4'-position and unsubstituted in the 5,5'-position are dissolved in 100 ml of DMF in a beaker, and 0.015 mol of triethyl orthoformate is added. After the addition of 0.01 mol of perchloric acid and heating to about 100° C., a dye salt which absorbs in the long-wave range forms, which salt is precipitated after the addition of ethanol and possibly a little ether and is then filtered off with suction. By reaction of the dye perchlorate with a solution of sodium polystyrenesulfonate, an aqueous solution of the respective cationically conductive material is obtained in the form of polystyrenesulfonate; this solution can be processed by spin-coating.

For example, the thiazole derivative VIt ($R^1$=$R^2$=phenyl and Y=CH) is prepared from the thiazole derivative VIq ($R^1$=$R^2$=phenyl) and triethyl orthoformate in the presence of perchloric acid in this manner.

NMR: (DMF-D$_7$):
a) 7.66 ppm (s) 1H
b) 7.77 ppm (t) 4H

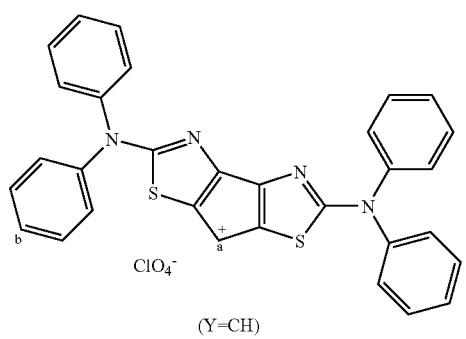

EXAMPLE 6

Synthesis of Thiazole Derivatives VI in the Form of Cationically Conductive Materials (Y=N)

0.01 mol of a dimeric thiazole derivative VIq or VIr bonded in the 4,4'-position and unsubstituted in the 5,5'- position are dissolved in 100 ml of THF in a beaker, and 0.015 mol of isoamyl nitrite is added. After the addition of 0.01 mol of perchloric acid with cooling and subsequent heating to about 50° C., a dye salt which absorbs in the long-wave range forms, which salt is precipitated after the addition of ethanol and possibly a little ether and is then filtered off with suction. By reacting the dye perchlorate with a solution of sodium polystyrenesulfonate, an aqueous solution of the respective cationically conductive material is obtained in the form of the polystyrenesulfonate; this solution can be processed by spin-coating.

For example, the thiazole derivative VIt ($R^1=R^2$=phenyl and Y=N) is prepared from the thiazole derivative VIq ($R^1=R^2$=phenyl) and isoamyl nitrite in the presence of perchloric acid in this manner.

NMR: (DMF-$D_7$):
a) 7.66 ppm (s) 1H

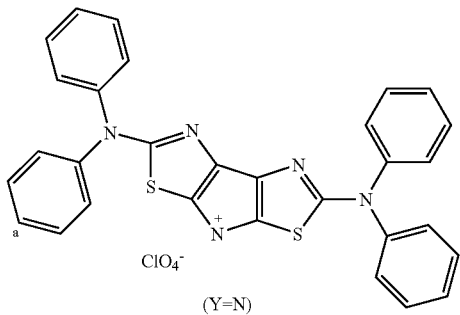

VIt (Y=N)

The invention claimed is:
1. A thiazole derivative having the following structure:

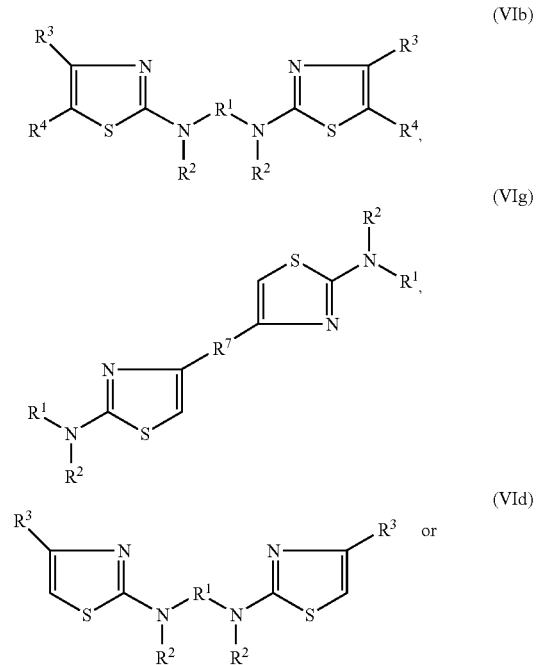

wherein $R^1$, $R^2$, $R^3$, and $R^4$ are selected from the group consisting of:
a) $R^1$, $R^2$, $R^3$, and $R^4$ are individual substituent groups, and $R^1$, $R^2$, and $R^3$ independently of one another are:
$R^1$ is a bifunctional (het)arylene system, which optionally comprises linearly or angularly fused or linked identical or different ring types, and peripheral hydrogen atoms optionally substituted by alkyl, alkoxy, phenoxy, dialkylamino or diphenylamino groups, wherein alkyl is $C_1$ to $C_6$;
$R^2$ is a monofunctional (het)aryl system, which optionally comprises linearly or angularly fused or linked identical or different ring types and peripheral hydrogen atoms optionally substituted by alkyl, alkoxy, phenoxy, dialkylamino or diphenylamino groups, wherein alkyl is $C_1$ to $C_6$; and
$R_3$ is
  i) a monofunctional (het)aryl system, which optionally comprises linearly or angularly fused or linked identical or different ring types and peripheral hydrogen atoms optionally substituted by alkyl, alkoxy, phenoxy, dialkylamino or diphenylamino groups, wherein alkyl is $C_1$ to C6,
  ii) $R^7$, $R^7$ being a chemical bond or a bifunctional (het)arylene system,

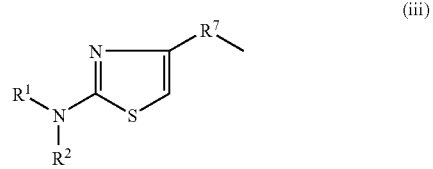

$R^7$ being a chemical bond or a bifunctional (het)arylene system, or

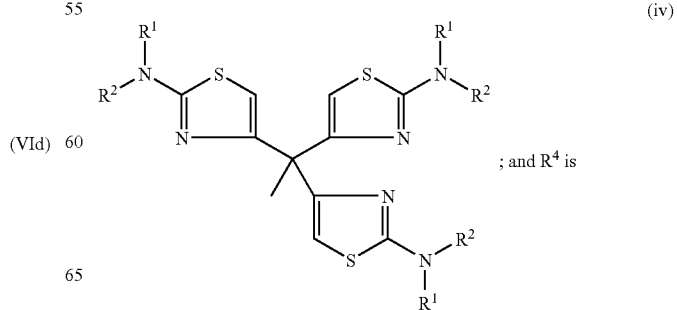

; and $R^4$ is

-continued

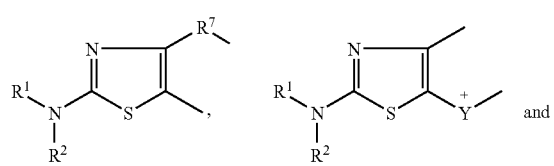

b) $R^1$ and $R^2$ are individual subsituent groups, and $R^3$ and $R^4$ together form an individual sustituent group, selected from the group consisting of:

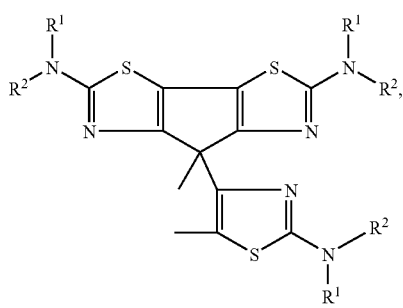

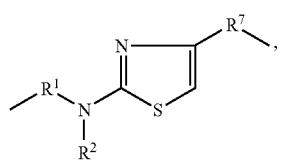

$R^7$ being a chemical bond or a bifunctional (het)arylene system, and Y being CH or N;

c) $R^2$ and $R^4$ are individual subsituent groups, and $R^3$ and $R^1$ together form an individual substituent group:

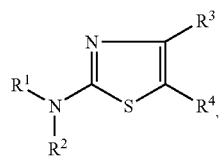

$R^7$ being a chemical bond or a bifunctional (het)arylene system;

d) $R^2$ and $R^3$ are individual subsituent groups, and $R^4$ and $R^1$ together form an individual substituent group:

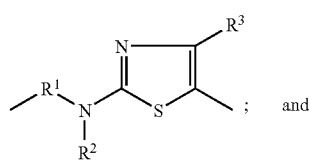

e) $R^2$ is an individual substituent group, and $R^3$ and $R^4$ together with $R^1$ form an individual substituent group:

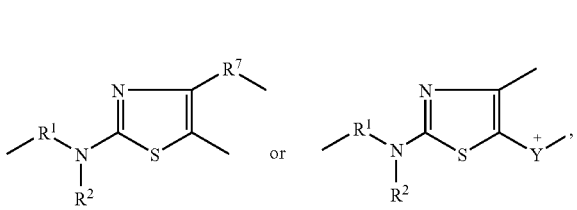

$R^7$ being a chemical bond or a bifunctional (het)arylene system, and Y being CH or N.

2. A 4substituted 2(N,N-di(het)arylamino)thiazole derivative of the structure

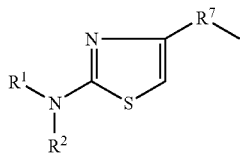

wherein $R^1$, $R^2$, $R^3$ and $R^4$ are selected from the group consisting of:

a) $R^1$, $R^2$, $R^3$ and $R^4$ are individual subsituent groups, and $R^1$, $R^2$, and $R^3$ independently of one another are each:

$R^1$ is
  a bifunctional (het)arylene system, which optionally comprises linearly or angularly fused or linked identical or different ring types, and peripheral hydrogen atoms optionally substituted by alkyl, alkoxy, phenoxy, dialkylamino or diphenylamino groups, wherein alkyl is $C_1$ to $C_6$;

$R^2$ is a monofunctional (het)aryl system, which optionally comprises linearly or angularly fused or linked identical or different ring types and peripheral hydrogen atoms optionally substituted by alkyl, alkoxy, phenoxy, dialkylamino or diphenylamino groups, wherein alkyl is $C_1$ to $C_6$; and $R^3$ is
  i) a monofunctional (het)aryl system, which optionally comprises linearly or angularly fused or linked identical or different ring types and peripheral hydrogen atoms optionally substituted by alkyl, alkoxy, phenoxy, dialkylamino or diphenylamino groups, wherein alkyl is $C_1$ to $C_6$,
  ii) $R^7$, $R^7$ being a chemical bond or a bifunctional (het)arylene system, (iii)

$R^7$ being a chemical bond or a bifunctional (het)arylene system, or

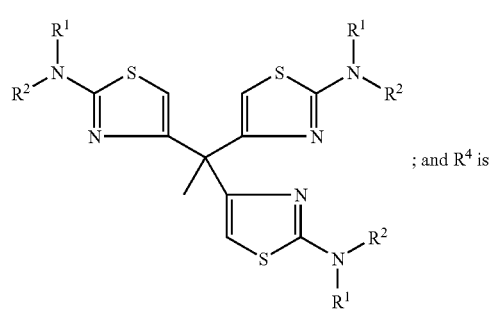

(iv)

; and $R^4$ is

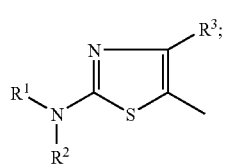

b) $R^1$ and $R^2$ are individual subsituent groups, and $R^3$ and $R^4$ together form an individual sustituent group, selected from the group consisting of:

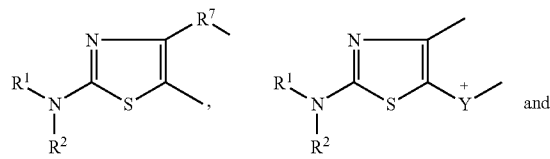

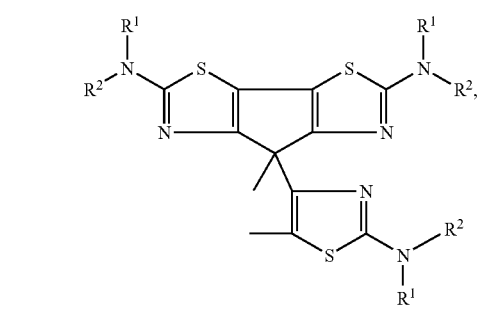

$R^7$ being a chemical bond or a bifunctional (het)arylene system, and Y being CH or N;

c) $R^2$ and $R^4$ are individual subsituent groups, and $R^3$ and $R^1$ together form an individual substituent group:

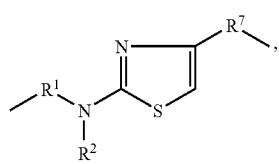

$R^7$ being a chemical bond or a bifunctional (het)arylene system;

d) $R^2$ and $R^3$ are individual subsituent groups, and $R^4$ and $R_1$ together form an individual substituent group:

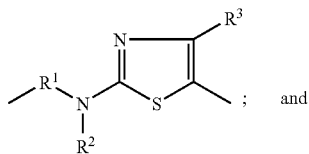

; and e) $R^2$ is an individual substituent group, and $R^3$ and $R^4$ together with $R^1$ form an individual substituent group:

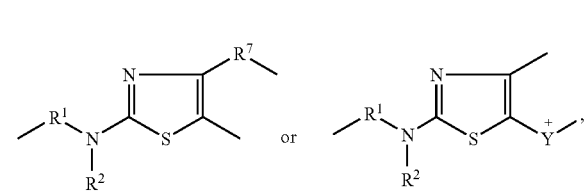

$R^7$ being a chemical bond or a bifunctional (het)arylene system, and Y being CH or N.

3. The thiazole derivative as claimed in claim 2, having the following structure:

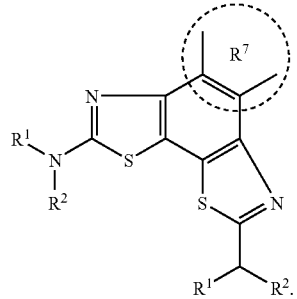

(VIm)

4. The thiazole derivative as claimed in claim 2, having the following structure:

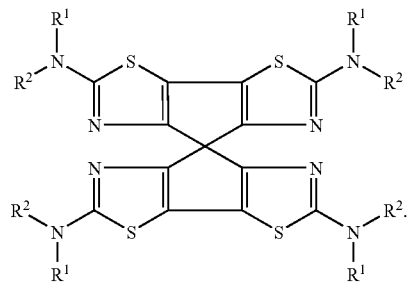

(VIp)

5. The thiazole derivative as claimed in claim 2, having the following structure:

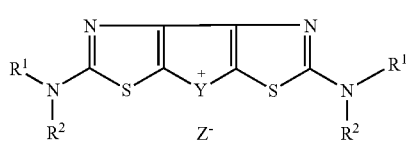

VI or

-continued

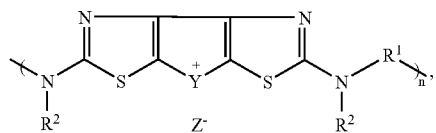

(VIu)

$Z^-$ being an anion, Y being —CH= or —NH= and n being an integer from 2 to 100.

6. The thiazole derivative as claimed in claim 2, having the following structure:

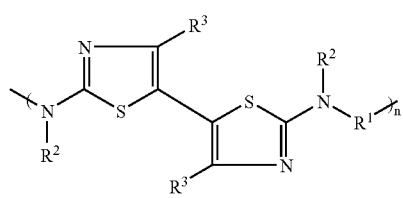

(VIf)

n being an integer from 2 to 100.

7. The thiazole derivative as claimed in claim 2, having a glass transition temperature (Tg) of at least 180° C.

8. An organic light-emitting diode which comprises at least one 4-substituted 2-(N,N-di(het)arylamino)thiazole derivative of the general structure

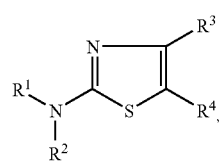

in which the following applies:

$R^1$, $R^2$ and $R^3$—independently of one another—are each a monofunctional (het)aryl system, i.e. a conjugated carbocyclic or heterocyclic ring system, which may also comprise linearly or angularly fused or linked identical or different ring types, it being possible for the peripheral hydrogen atoms optionally to be substituted by alkyl, alkoxy, phenoxy, dialkylamino or diphenylamino groups (alkyl=$C_1$ to $C_6$);

$R^1$ may furthermore be a corresponding bifunctional (het)arylene system, i.e. a conjugated carbocyclic or heterocyclic ring system, which may also comprise linearly or angularly fused or linked identical or different ring types, it being possible for the peripheral hydrogen atoms optionally to be substituted by alkyl, alkoxy, phenoxy, dialkylamino or diphenylamino groups (alkyl=$C_1$ to $C_6$);

$R^3$ may furthermore be $R^7$, $R^7$ being a chemical bond or a bifunctional (het)arylene system, or $R^3$ may be one of the following groups:

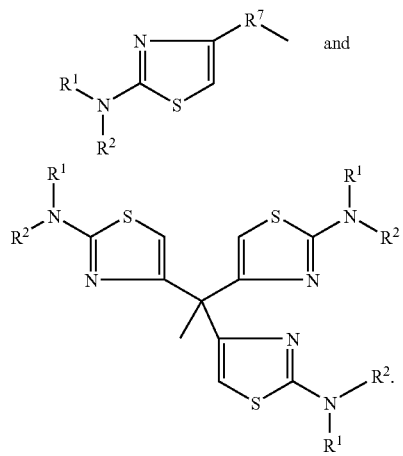

and

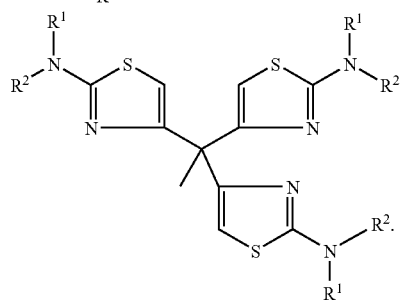

$R^7$ being a chemical bond or a bifunctional (het)arylene system;

$R^4$ may also be H or

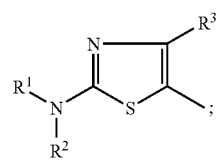

the following may furthermore be the case:
$R^3$ and $R^4$ together form one of the following groups:

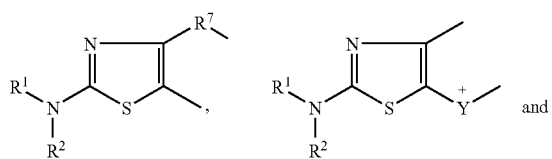

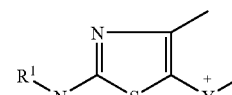

and

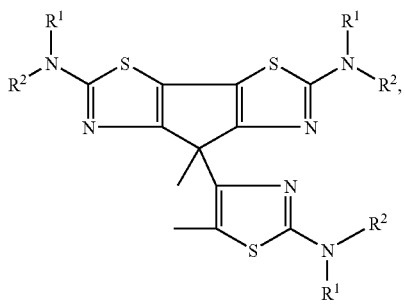

$R^3$ together with $R^1$ forms the following polymer segment:

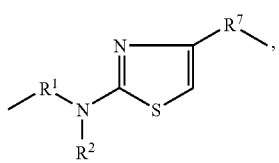

$R^4$ together with $R^1$ forms the following polymer segment:

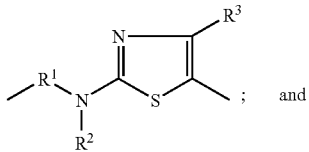
; and $R^4$ and $R^3$ together with $R^1$ form the following polymer segments:

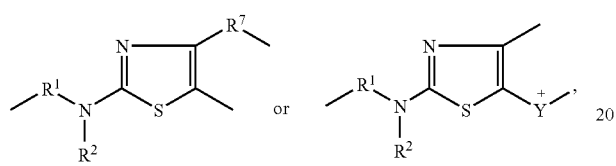

Y in each case being CH or N, as a charge transport layer and/or emitter layer, the electronic properties of the (het)aryl substituent determining whether the thiazole derivative has electron-transporting or hole-transporting activity.

9. An organic light-emitting diode comprising at least one 4-substituted 2-(N,N-di(het)arylamino)thiazole derivative of the structure:

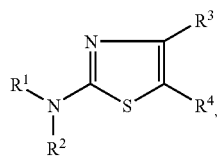

wherein $R^1$, $R^2$, and $R^3$ independently of one another are each:

$R^1$ is
  i) a monofunctional (het)aryl system or
  ii) a corresponding bifunctional (het)arylene system, which optionally comprises linearly or angularly fused or linked identical or different ring types, and peripheral hydrogen atoms substituted by alkyl, alkoxy, phenoxy, dialkylamino or diphenylamino groups, wherein alkyl is $C_1$ to $C_6$;

$R^2$ is a monofunctional (het)aryl system, which optionally comprises linearly or angularly fused or linked identical or different ring types and peripheral hydrogen atoms substituted by alkyl, alkoxy, phenoxy, dialkylamino or diphenylamino groups, wherein alkyl is $C_1$ to $C_6$;

$R^3$ is
  i) a monofunctional (het)aryl system, which optionally comprises linearly or angularly fused or linked identical or different ring types and peripheral hydrogen atoms substituted by alkyl, alkoxy, phenoxy, dialkylamino or diphenylamino groups, wherein alkyl is $C_1$ to $C_6$,
  ii) $R^7$, $R^7$ being a chemical bond or a bifunctional (het)arylene system,

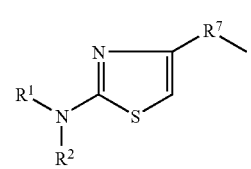
(iii)

$R^7$ being a chemical bond or a bifunctional (het)arylene system, or

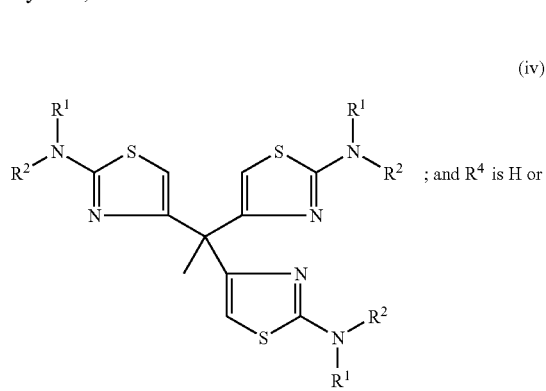
(iv)

; and $R^4$ is H or

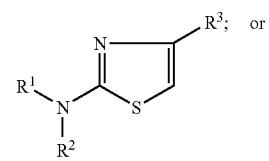
; or $R^3$ and $R^4$ together is selected from the group consisting of:

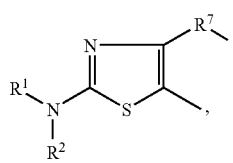
,
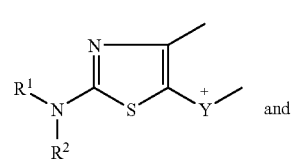
and

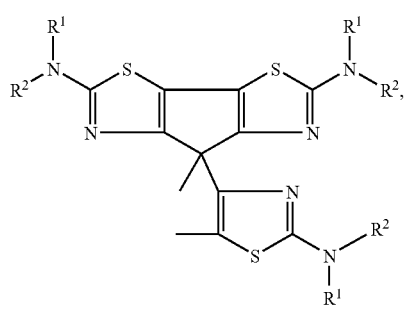

$R^7$ being a chemical bond or a bifunctional (het)arylene system, and Y being CH or N; or $R^3$ and $R^1$ together is

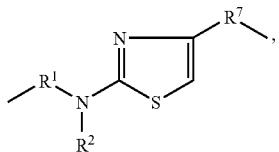

$R^7$ being a chemical bond or a bifunctional (het)arylene system; or $R^4$ together with $R^1$ is

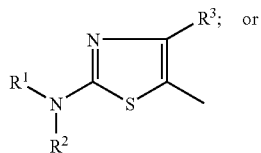

$R^4$ and $R^3$ together with $R^1$ is

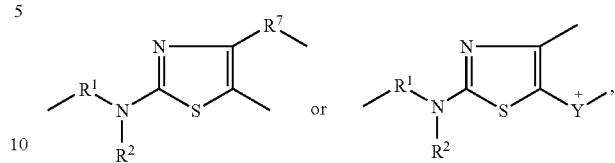

$R^7$ being a chemical bond or a bifunctional (het)arylene system, and Y being CR or N, as a charge transport layer and/or emitter layer, the electronic properties of the (het)aryl substituent determining whether the thiazole derivative has electron-transporting or hole-transporting activity.

* * * * *

UNITED STATES PATENT AND TRADEMARK OFFICE
CERTIFICATE OF CORRECTION

PATENT NO. : 7,357,989 B2 Page 1 of 1
APPLICATION NO. : 10/343992
DATED : April 15, 2008
INVENTOR(S) : Horst Hartmann et al.

It is certified that error appears in the above-identified patent and that said Letters Patent is hereby corrected as shown below:

On the title page, Item [56], under U.S. PATENT DOCUMENTS insert:
--5,639,770 A 6/1997 Chihiro et al.--.

Signed and Sealed this

Twenty-fifth Day of May, 2010

David J. Kappos
*Director of the United States Patent and Trademark Office*